United States Patent [19]

Harbour

[11] 4,149,415
[45] Apr. 17, 1979

[54] APPARATUS FOR SENSING MOVING PARTICLES OR SMALL MOVING OBJECTS

[75] Inventor: John Harbour, Chippenham, England

[73] Assignee: Probe Engineering Company Limited, Cirencester, England

[21] Appl. No.: 707,840

[22] Filed: Aug. 9, 1976

[51] Int. Cl.$^2$ ............................................. G01N 29/00
[52] U.S. Cl. .......................... 73/432 PS; 56/DIG. 15
[58] Field of Search ............. 73/432 PS, 194 M, 228; 340/261, 267; 56/DIG. 15; 310/328, 329

[56] References Cited

U.S. PATENT DOCUMENTS

| | | | |
|---|---|---|---|
| 2,386,279 | 10/1945 | Tibbetts | 310/329 |
| 2,578,620 | 12/1951 | Wilhelm | 310/328 |
| 3,515,144 | 6/1970 | Morrison | 56/DIG. 15 |
| 3,853,199 | 12/1974 | Hirashima et al. | 200/61.08 |
| 3,939,846 | 2/1976 | Drozhzhin et al. | 56/DIG. 15 |
| 4,004,289 | 1/1977 | Kirk | 56/DIG. 15 |
| 4,036,065 | 7/1977 | Strelioff et al. | 73/432 R |
| 4,047,427 | 9/1977 | Young | 73/141 A |

*Primary Examiner*—Anthony V. Ciarlante
*Attorney, Agent, or Firm*—Andrus, Sceales, Starke & Sawall

[57] ABSTRACT

A detector for sensing the presence of grain in straw or chaff discharged from a combine has an elongated flat target plate extending across the machine. It is mounted on a relatively massive base through the intermediary of longitudinal resilient strips, which allow transverse bending. Transducers mounted on the reverse side of the plate provide an output from which sharp, grain impact signals can be filtered. The resilient strips are best arranged along nodes of a selected harmonic, preferably the second, of the transverse bending vibrations of the plate. The detector can be used generally for sensing small particles.

4 Claims, 3 Drawing Figures

APPARATUS FOR SENSING MOVING PARTICLES OR SMALL MOVING OBJECTS

BACKGROUND OF THE INVENTION

Field of the Invention

This invention relates to apparatus for sensing or detecting small moving particles or small moving objects, and is particularly though not exclusively applicable to apparatus for sensing or detecting cereal grain.

SUMMARY OF THE PRESENT INVENTION

The invention may be used to sense the grain lost with the straw or chaff from a combine harvester.

The invention is concerned with particle detectors of the type having a target on which the particles impinge, and an acoustic transducer for detecting consequent vibrations of the target. An earlier example is described in the Specification of our U.K. Pat. No. 1,384,882 in which the target is an elongated cylindrical drum, filled with liquid, and with microphones at one or each end. This has given good results, but it does have a drawback in that its sensitivity varies across its width. Referring to FIG. 1 of the accompanying drawing, which shows diagrammatically such a sensor in cross-section, it will be seen that for particles moving in the direction of the arrow, those impinging on the cylinder over the central zone A will be striking almost normally against the surface, and therefore providing firm impacts giving full sensitivity, while particles impinging towards the edge zones B will strike only glancing blows and will not produce such a good response.

It would be better to have a sensor in the form of a flat strip of uniform sensitivity across its width, for then the whole area would give a useful response and sample a larger proportion of the straw stream for a given obstruction. It is an object of this invention to provide such a sensor.

According to the present invention there is provided apparatus for sensing moving particles or small moving objects, comprising an elongated plate one side of which is a target for said objects, a relatively massive base, resilient strips interposed between the base and the other side of the plate, and transducer means mounted on said other side of the plate between resilient strips.

Preferably the strips are arranged along nodes of a selected harmonic of transverse bending vibrations of the plate. Conveniently the second harmonic is selected, and then there are three resilient mounting strips with two transducers mounted between respective adjacent pairs of strips. For reasons to be explained it is advantageous to mount the transducers with opposite polarities.

Brief Description of the Drawing

For a better understanding of the invention one constructional form will now be described, by way of example, with reference to the remaining figures of the accompanying drawing, in which.

DETAILED DESCRIPTIN OF THE PREFERRED EMBODIMENT

Figure 1:
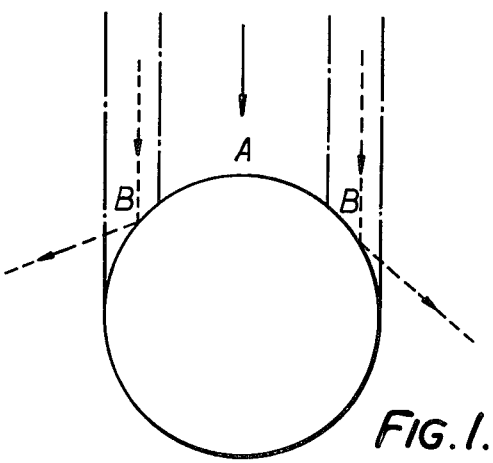
FIG. 1 is a diagrammatic view of a prior art sensor
Figure 2:
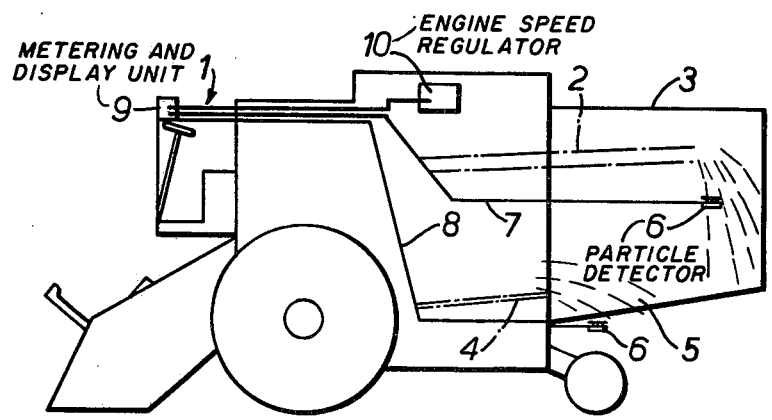
FIG. 2 is a diagrammatic side elevation of a combine harvester with two grain detector elements.

Combine harvesters are well known and will not be described in detail. In FIG. 2 the harvester has a driving position 1 at the front of the machine and conventional mechanism for cutting the grain and delivering it to the straw and chaff separators. There is a straw walker 2 arranged to discharge straw from beneath a hood 3 at the rear of the machine. Below the straw walker is a grain sieve system 4 designed to separate grain from the chaff and to discharge the chaff at a zone 5, also within the hood 3. Particle detecting elements 6 are positioned within the hood immediately below the output end of the straw walker 3 and immediately below the discharge end of the grain sieve 4. Each detector extends horizontally across the full width of the respective straw walker or grain sieve, so that a proportion or constant fraction of the grain that is lost from either of these devices will impinge on one of the target elements and produce an output signal. The detectors are connected by cables 7 and 8 to a metering and display unit 9 positioned in front of the driving position so as to be readily visible. The unit 9 may include counting or integrating devices to provide an output indication corresponding to the rate at which grain is being lost. Another output from the metering unit 9 is coupled to an automatic engine speed regulator 10 so that the speed of the combine harvester can be controlled in response to the sensed grain loss.

The function of the detectors is to distinguish between grain and the straw and chaff. In the case of the walker sensor, for instance, the weight of the straw and the number of individual straws deflected by the sensor far outweighs the weight and numbers of grain. However the grains are denser and harder, so that individual grain impacts give impulses of shorter duration. The frequency spectrum of the short duration impulses contains a greater proportion of high frequencies and these can be isolated by electrical filters. However, vibration resonances of the sensor also serve to emphasise certain frequencies. Broadly, the larger the sensor, the lower the frequency of these mechanical vibration resonances. Thus for a large area sensor, further electrical filtering would have to be applied to reduce the effect of straw impact. There is also the problem that, in practice, energy is absorbed by various modes of resonant vibrations and the energy available in the higher frequencies is reduced.

Mechanical damping of the sensor can reduce the predominance of low frequency vibrations, but it also tends to absorb vibrational energy before it can spread from the point of impact to the point at which the vibration is sensed. Therefore the sensitivity to impact is low in parts of the sensor remote from the transducer. In order to achieve more uniform resonance, a high 'Q' factor of the resonant vibrations is required, for the higher that factor is the greater the number of cycles of vibration executed for a given factor of decay in amplitude. However, if there are a large number of impacts per unit time to be resolved, a low Q factor is desirable, namely one that is associated with a rapid decay in the resonance. Alternatively and preferably a high resonant frequency F can be adopted so that although Q may be high, the ratio Q/F is also high.

As well as these requirements of a high 'Q' factor, a high Q/F ratio and a high resonant frequency F to resolve adequately the impacts of grain from those of chaff and straw, a large area sensor is needed to respond to grain loss across the width of the combine. However, a high resonant frequency is not normally compatible with a large size sensor.

Figure 3:
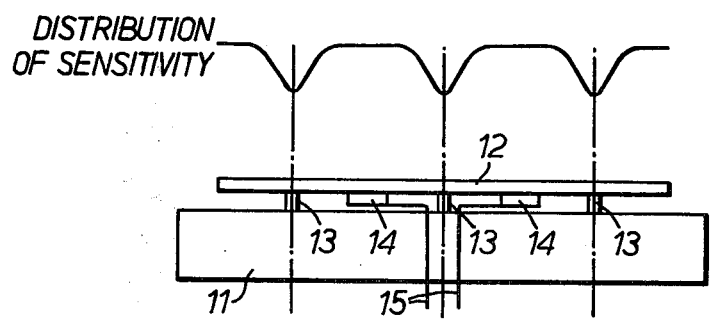
FIG. 3 is a cross-section of a detector according to the invention, showing a related response characteristic.

Referring now to FIG. 3, there is shown a sensor or detector which, as well as offering a good area facing the direction of straw or chaff flow, is mounted in such a way that the high frequencies can be effectively isolated.

The detector comprises a wooden base in the form of a beam 11 which extends across the discharge stream and has on the side facing that stream an elongated aluminum plate 12 mounted by three hard rubber strips 13 extending longitudinally of the detector and situated at the nodes of the second harmonic of transverse vibrational bending of the plate 12. Centrally disposed between adjacent pairs of strips 13 and mounted on the underside of the plate 2 are transducers 14 of opposite polarities, and with leads 15 to an amplifier and further circuitry (not shown) but which is preferably of the kind described in our co-pending application Ser. No. 31,876/75. As an example of dimensions, the size of the cross-section of base 11 may be of the order of 100×25 mm while the superimposed plate 12 may be of the order of 6 mm thick. This mounting of the sensing plate 12 results in a very selective transmission of frequencies to the amplifier. The resilient mounting at the three nodal lines and the relatively massive wooden base will severely damp many other transverse modes, especially odd harmonic modes, for example the fundamental, third fifth and so on. Furthermore, with the transducers mounted with opposite polarities, similar and equal bending movements due to vibrations in the fundamental and odd harmonic modes cancel out. However, the opposite bending forces experienced by the transducers at the second harmonic mode (and at odd multiples thereof) are additive. Longitudinal bending modes of vibration perpendicular to the plane of the sensor are completely cancelled. These modes are of low frequency and large amplitude due to combine engine and suspension vibration. Their cancellation will greatly reduce the isolation required.

With such a detector of the size indicated, a high resonant frequency has been observed of approx. 12 KHz. This shows a good 'Q' factor of the order of 20 to 50, which has been found to give a substantially uniform response over a length of about a meter. It permits the resolution of impulses with less than 5 mS separation. A similar device but with just two strip supports has been compared with the sensor described, and this vibrates at about 5 KHz. While it shows a slightly higher 'Q' factor, the impulse separation interval is now of the order of 10 mS.

It will be appreciated that the sensitivity of such a sensor is not uniform, varying across the width of the sensor as indicated by the graph at the top of FIG. 3. The sensitivity reduces virtually to zero at the nodal lines. However, this is not a disadvantage in practice for between the nodes the response is reasonably uniform and there are no areas of exceptionally high sensitivity. Along its length the sensor is very uniformly sensitive.

The absence of liquid will allow easier mounting and use of such sensors, and low susceptibility to external vibration will allow a simple mounting, even to moving parts; for example to the shoe of a sieve or a walker.

It will be understood that these sensors can be employed in other applications where the detecting of hard particles is required and where particle flow rates are to be detected.

I claim:

1. Apparatus for sensing moving particles or small moving objects, comprising an elongated plate one side of which is a target for said objects, a relatively massive base, parallel, regularly spaced resilient strips interposed between the base and the other side of the plate and extending longitudinally thereof, the spacing of the strips being such that they coincide with nodes of a selected harmonic of transverse bending vibrations of the plate, and transducer means mounted on said other side of the plate between resilient strips.

2. Apparatus as claimed in claim 1, wherein the selected harmonic is the second, there being three said resilient strips with two transducers mounted between respective adjacent pairs of strips.

3. Apparatus as claimed in claim 2, wherein the transducers are mounted with opposite polarities.

4. A combine harvester equipped with apparatus as claimed in claim 1 and arranged for detecting waste grain.

* * * * *